(12) United States Patent
Stever et al.

(10) Patent No.: US 9,370,623 B2
(45) Date of Patent: Jun. 21, 2016

(54) DRIVE ASSEMBLY FOR A MEDICATION DELIVERY DEVICE AND MEDICATION DELIVERY DEVICE COMPRISING A DRIVE ASSEMBLY

(71) Applicant: SANOFI-AVENTIS DEUTSCHLAND GMBH, Frankfurt am Main (DE)

(72) Inventors: Tobias Stever, Frankfurt am Main (DE); Ngoc-Jane Lam, Frankfurt am Main (DE); Ulrik Jakobi, Frankfurt am Main (DE); Nils Basso, Frankfurt am Main (DE); Olaf Zeckai, Weinheim (DE); Meinolf Werner, Worms (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 87 days.

(21) Appl. No.: 14/362,535

(22) PCT Filed: Dec. 5, 2012

(86) PCT No.: PCT/EP2012/074414
§ 371 (c)(1),
(2) Date: Jun. 3, 2014

(87) PCT Pub. No.: WO2013/083589
PCT Pub. Date: Jun. 13, 2013

(65) Prior Publication Data
US 2014/0343510 A1   Nov. 20, 2014

Related U.S. Application Data

(60) Provisional application No. 61/598,497, filed on Feb. 14, 2012.

(30) Foreign Application Priority Data

Dec. 8, 2011   (EP) .................................... 11192527

(51) Int. Cl.
*A61M 5/315*   (2006.01)
*A61M 5/24*   (2006.01)

(52) U.S. Cl.
CPC ............. *A61M 5/31501* (2013.01); *A61M 5/24* (2013.01); *A61M 5/31543* (2013.01);
(Continued)

(58) Field of Classification Search
CPC ............ A61M 5/315; A61M 5/31501; A61M 5/31511; A61M 2005/3152; A61M 5/31525; A61M 5/31528; A61M 5/31543
See application file for complete search history.

(56) References Cited

U.S. PATENT DOCUMENTS

| | | | |
|---|---|---|---|
| 2009/0275916 A1 | 11/2009 | Harms et al. | |
| 2010/0114025 A1* | 5/2010 | Moller | A61M 5/20 604/135 |
| 2011/0054412 A1* | 3/2011 | Eich | A61M 5/20 604/207 |

FOREIGN PATENT DOCUMENTS

| | | | | |
|---|---|---|---|---|
| CH | WO 2009105909 A1 * | 9/2009 | ............. | A61M 5/20 |
| CN | 101420997 | 4/2009 | | |

(Continued)

OTHER PUBLICATIONS

International Search Report for Int. App. No. PCT/EP2012/074414, completed Feb. 15, 2013.
(Continued)

*Primary Examiner* — Kami A Bosworth
*Assistant Examiner* — Nilay Shah
(74) *Attorney, Agent, or Firm* — McDonnell Boehnen Hulbert & Berghoff LLP

(57) ABSTRACT

A drive assembly for a medication delivery device is provided, comprising a piston rod which is movable from a start position to an end position for medication delivery and resettable from the end position to the start position. The drive assembly further comprises a guide member, being in engagement with the piston rod, and an impeding element for impeding a movement of the guide member during a reset of the piston rod and thereby impeding the reset of the piston rod. Furthermore, a medication delivery device comprising the drive assembly is disclosed.

11 Claims, 4 Drawing Sheets

(52) U.S. Cl.
CPC ...... *A61M 5/31551* (2013.01); *A61M 5/31585* (2013.01); *A61M 5/31593* (2013.01); *A61M 5/315* (2013.01); *A61M 5/31511* (2013.01); *A61M 5/31528* (2013.01); *A61M 2005/2407* (2013.01); *A61M 2005/2488* (2013.01); *A61M 2005/3152* (2013.01)

(56) References Cited

FOREIGN PATENT DOCUMENTS

| | | | | |
|---|---|---|---|---|
| CN | 102083489 | 6/2011 | | |
| GB | 482306 A | * | 3/1938 | .............. B64C 25/62 |
| WO | 93/07922 | 4/1993 | | |
| WO | 2007/118907 | 10/2007 | | |
| WO | 2009/132778 | 11/2009 | | |
| WO | 2010/063687 | 6/2010 | | |
| WO | 2010/112561 | 10/2010 | | |
| WO | 2010/139640 | 12/2010 | | |
| WO | 2011/039203 | 4/2011 | | |
| WO | 2011/068531 | 6/2011 | | |

OTHER PUBLICATIONS

Chinese Office Action for CN Application No. 20128006039837, issued Nov. 2, 2015.

* cited by examiner

DRIVE ASSEMBLY FOR A MEDICATION DELIVERY DEVICE AND MEDICATION DELIVERY DEVICE COMPRISING A DRIVE ASSEMBLY

CROSS REFERENCE TO RELATED APPLICATIONS

The present application is a U.S. National Phase Application pursuant to 35 U.S.C. §371 of International Application No. PCT/EP2012/074414 filed Dec. 5, 2012, which claims priority to European Patent Application No. 11192527.7 filed Dec. 8, 2011 and U.S. Provisional Patent Application No. 61/598,497, filed Feb. 14, 2012. The entire disclosure contents of these applications are herewith incorporated by reference into the present application.

TECHNICAL FIELD

The present disclosure relates to a drive assembly for a medication delivery device.

BACKGROUND

A medication delivery device comprising a drive assembly is known from patent application WO 2009/132778 A1. This application relates to a medication delivery device comprising a multi-dose medication cartridge, which can be replaced when the medication has been fully dispensed.

SUMMARY

It is an object of the present invention to provide a drive assembly for a medication delivery device having improved properties.

According to one aspect of the disclosure, a drive assembly for a medication delivery device is provided. The drive assembly comprises a piston rod which is movable from a start position to an end position for medication delivery and resettable from the end position to the start position. Furthermore, the drive assembly comprises a guide member being in engagement with the piston rod. Preferably, the guide member is in engagement with the piston rod both during medication delivery and during a reset of the piston rod.

Accordingly, the drive assembly may have an operational state, in which a movement of the piston rod from the start position to the end position is enabled. In the operational state, a movement from the end position to the start position may be disabled. Furthermore, the drive assembly may have a reset state, in which a movement of the piston rod from the end position to the start position is enabled.

Additionally, the drive assembly comprises an impeding element. The impeding element may be configured to impede a movement of the guide member during a reset of the piston rod. Particularly, the impeding element may impede a rotation of the guide member. By impeding a movement of the guide member during a reset of the piston rod, the impeding element may impede a movement of the piston rod.

Preferably, the impeding element is coupled to the guide member such that in a reset state of the drive assembly the guide member may only be moved against a resistance, in particular a force exerted on the guide member by the impeding element, for example a friction force. Preferably, the force exerted on the guide member is larger than the gravitational force of the piston rod. Thereby, an unhindered movement of the piston rod, in particular caused by the weight of the piston rod, is prevented by the impeding element.

Preferably, in the reset state, the impeding element exerts a force, e.g. a friction force, on the guide member. The force may be exerted on the guide member at least during a movement of the piston rod from the end position to the start position. The force may also be exerted on the guide member in the operational state, in particular during a movement of the piston rod from the start position to the end position. Preferably, the force does not lead to a significant increase of the force required for the delivery of a medication.

Accordingly, "impeding a movement" preferably leads to an increase of a force required to move a member of the drive assembly, particularly the guide member.

Preferably, the impeding element is fixed relative to a body part of the drive assembly, such that a relative movement between the impeding element and the body part of the drive assembly is prevented. When the drive assembly is assembled with a medication delivery device, the body part may be fixed to or may be part of a main body of the medication delivery device.

In a preferred embodiment, the impeding element comprises at least one locking member for fixing the impeding element to the body part. As an example, the locking member may be snap-fitted to the body part. In particular, the impeding element may be fixed with respect to the body part at least when the drive assembly is in the reset state. Thereby, a rotation of the impeding element during a movement of the guide member may be prevented.

Additionally or alternatively, the guide member may be axially fixed with respect to the body part of the drive assembly.

In a preferred embodiment, the drive assembly may be used in an injection device. Preferably, the medication delivery device may be a pen-type device. The medication delivery device may be configured to deliver a medical fluid. In particular, the medication may be insulin.

The term "piston rod" is preferably used for a component of the drive assembly, which is configured to carry out a movement towards a dispensing end of a medication delivery device and, thereby, cause a medication to be dispensed from the device. In particular, a movement from the start position to the end position may correspond to a movement towards the dispensing end.

The start position may be a position of the piston rod wherein the piston rod is furthest away from the dispensing end of the device when the drive assembly is assembled with the medication delivery device. The end position may be a position wherein the piston rod is closer to the dispensing end than in the start position, in particular closest to the dispensing end of the medication delivery device. Accordingly, a movement from the end position to the start position may be a movement in a proximal direction. The proximal direction is a direction towards the proximal end of the medication delivery device. The term "proximal end" designates that end of the assembly or of the device which is or is to be arranged furthest away from a dispensing end of the device. Correspondingly, a movement from the start position to the end position, for example during the delivery of a medication, may be a movement in a distal direction. The distal direction is a direction towards the dispensing end of the medication delivery device.

The piston rod may be configured to act on a bung or a piston in a medication container, for example a cartridge, causing a medication to be dispensed from the container. The piston rod may be configured for carrying out a combined axial and rotational movement during a dispense of a medication. As an example, the piston rod may be configured as a simple rod. Preferably, the piston rod is configured as a leadscrew. The leadscrew may comprise at least one threaded section for engaging with a corresponding part of the medication delivery device.

Preferably, the guide member and the piston rod are threadedly engaged.

The guide member may comprise or may be configured as a nut member. The nut member may comprise a threaded section being in engagement with the piston rod. During dispense of a medication, the piston rod may rotate through the nut member towards the distal end of the medication delivery device.

In one embodiment, the piston rod comprises at least two threaded sections. Preferably, the threaded sections have an opposite sense of rotation. The piston rod may be in threaded engagement with the guide member, in particular a nut member, by a first threaded section. By a second threaded section, the piston rod may be in engagement with a further member of the medication delivery device, in particular a drive member. The drive member may be configured to exert a force on the piston rod and thereby cause a movement of the piston in a distal direction for medication delivery.

Preferably, during a movement of the piston rod from the start position towards the end position, the guide member may be fixed with respect to a body part of the drive assembly, in particular rotationally fixed to the body part. Thereby, when the drive assembly is used in a medication delivery device, the guide member may be fixed with respect to a main body of the device.

In a preferred embodiment, the guide member comprises at least one engagement member. Preferably, the engagement member is configured to fix, in particular rotationally fix the guide member with respect to the body part of the drive assembly.

The engagement member may comprise at least one tooth. The tooth may be located at the circumference of the guide member. In a preferred embodiment, the engagement member comprises a plurality of teeth, in particular located at the circumference of the guide member.

Preferably, the engagement member is configured to engage with the body part of the drive assembly. Preferably, an engagement exists in the operational state of the drive assembly, in particular when a receptacle is attached to the main body of the device. Thereby, a rotation of the guide member may be prevented when the receptacle is attached to the main body. Preferably, in the reset state the guide member is disengaged from the body part, in particular when a receptacle is detached from the main body of the medication delivery device. Thereby, a rotation of the guide member may be enabled.

Preferably, the body part is configured to be fixed to the main body of the medication delivery device. Thereby, the body part may rotationally lock the guide member with respect to the main body.

Alternatively, the guide member may be configured to be directly locked to the main body. For example, the main body may comprise grooves into which the engagement member may engage.

As an example, the guide member may be rotationally locked with respect to the body part by a spring means. For example, the spring means may be configured to engage with the engagement member of the guide member in the operational state, such that a rotation of the guide member is prevented.

Particularly, the guide member may be fixed with respect to the body part of the drive assembly during the delivery of a medication. In the case that the piston rod comprises two threaded sections and the guide member is rotationally fixed with respect to the body part of the drive assembly, a rotation of the piston rod in a proximal direction may be prevented by the two threaded sections of the piston rod being in engagement with the guide member and the drive member, respectively.

The guide member may be rotationally fixed to the body part of the drive assembly by a locking member. Preferably, the locking member is engaged with the guide member, and thereby locks the guide member during the delivery of a medication.

The piston rod may be configured to be reset to the start position when the medication from the cartridge has been partially or fully dispensed. By resetting the piston rod, the medication delivery device may be prepared for the insertion of a new cartridge, after the used cartridge has been replaced.

Preferably, during a reset of the piston rod, the guide member is movable, in particular rotatable, with respect to the body part of the drive assembly. Particularly, the locking member may be disengaged from the guide member for a reset of the piston rod such that a movement, in particular a rotation, of the guide member with respect to the body part is enabled. Preferably, the drive assembly is configured such that when the guide member is enabled to move, in particular enabled to rotate, relative to the body part, a movement of the piston rod in a proximal direction is enabled.

Accordingly, in the operational state of the drive assembly, a movement of the guide member may be disabled and in the reset state of the drive assembly, a movement of the guide member may be enabled.

To enable a reset of the piston rod, a receptacle which may be attached to a main body of the medication delivery device during delivery of a medication may have to be detached from the main body.

By the detachment of the receptacle, the guide member may be enabled to carry out a movement with respect to the body part of the drive assembly. In particular, when the guide member is disengaged from the locking member, it may rotate with respect to the body part. Thereby, the piston rod may be enabled to be moved towards the start position.

Accordingly, the drive assembly may be configured to change from its operational state to its reset state by a disengagement of a receptacle from a main body of the medication delivery device.

In a reset operation the piston rod may be rotated back to the start position. In particular, the piston rod may carry out a combined rotational and linear movement. During a rotation of the piston rod to the start position, the piston rod may be screwed through a thread of the guide member. When the piston rod rotates through the guide member towards the start position, the guide member may rotate with an opposite sense of rotation with respect to the body part. In a further embodiment, the movement of the piston rod during a reset may be purely linear and a rotational movement may be prevented.

Preferably, the impeding element prevents an unhindered movement, in particular an unhindered rotation, of the guide member during reset. Preferably, the guide member has to be moved against a resistance, in particular a force exerted on the guide member by the impeding element. In particular, during a movement of the guide member, the impeding element may exert a friction force on the guide member.

In particular, an unhindered rotation of the guide member and, thereby, an unhindered movement of the piston rod may be prevented when the receptacle is removed from the main body of the medication delivery device and when the drive assembly is in a reset state. In particular, the impeding element may impede a movement of the piston rod when the receptacle is unintentionally removed from the main body of the medication delivery device. In particular, a movement caused by a gravitational force of the piston rod may be prevented.

Preferably, the impeding element comprises at least one resilient element.

In a preferred embodiment, the impeding element, in particular the resilient element, is biased towards the guide member. Thereby, tolerances between the guide member and the impeding element may be compensated. Additionally, it may be ensured that a force is exerted on the guide member at any time during a reset of the piston rod.

Preferably, the resilient element acts on the guide member, in particular on a circumference of the guide member. Particularly, the resilient element may exert a force on the guide member. The force exerted on the guide member by the resilient element may be an elastic force. During a movement of the guide member, the elastic force may cause a friction force being exerted on the guide member. Thereby, the force for moving the guide member, particularly for resetting the piston rod, may be increased.

In a preferred embodiment, the impeding element comprises a contact surface being in contact with the guide member. In particular, the resilient element may comprise a contact surface being in contact with the guide member, for example at the circumference of the guide member.

In a preferred embodiment, the impeding element comprises a plurality of resilient elements.

Preferably, the resilient elements are located rotationally symmetric around the guide member. The resilient elements may be arranged such that the guide member is uniformly loaded along its circumference.

As an example, the impeding element may comprise two resilient elements being arranged opposite to each other.

In a preferred embodiment, the force exerted on the guide member by the impeding element is directed in a radial direction with respect to a longitudinal axis of the drive assembly. Particularly, the impeding element is biased towards the guide member in a radial direction.

The amount of resistance against which the guide member may have to be moved during a reset of the piston rod, in particular the friction force, may be determined by the elasticity of the resilient element. In particular, the amount of the friction force may be increased by decreasing the elasticity of the resilient element. The amount of friction force may be decreased by increasing the elasticity of the resilient element.

In a preferred embodiment, the impeding element, particularly the resilient element, comprises a cut-out. Preferably, the elasticity of the resilient element is affected by the shape of the cut-out.

In particular, the material thickness of the resilient element may be affected by the shape of the cut-out. For example, by increasing the material thickness of the resilient element, the elasticity of the same may be reduced. For increasing the material thickness the size of the cut-out may have to be decreased. Thereby, the force exerted on the guide member may be increased.

For example, the cut-out may comprise the shape of a triangle. In a further embodiment, the cut-out may comprise the shape of a rectangle. Alternatively, the cut-out may comprise the shape of a circle.

In a preferred embodiment, the impeding element is configured to not engage with the engagement member of the guide member. Particularly, the resilient element may be configured to not engage with the engagement member, respectively with teeth located at the circumference of the guide member. As an example, the contact surface of the impeding element may have a width larger than a gap between two adjacent engagement members of the guide member. Thereby, a jamming of the impeding element in the gap between two engagement members of the guide member may be prevented. During a movement of the guide member in a reset operation of the piston rod, the impeding element may slide over the engagement member, in particular over the teeth.

According to a further aspect of the present disclosure, a medication delivery device is provided, the medication delivery device comprising a drive assembly. The drive assembly may comprise any structural and functional features as described above.

The medication delivery device may comprise a main body. Preferably, the body part of the drive assembly is provided by the main body or is fixed to the main body.

The medication delivery device may be an injection device. Preferably, the medication delivery device is a pen-type device. Preferably, the medication delivery device is configured to dispense a medication, in particular a medical fluid. Particularly the medication may be insulin. Preferably, the medication delivery device is a reusable device.

The medication delivery device may comprise a medication receptacle being configured to receive a cartridge containing a medicament.

In a preferred embodiment, the medication delivery device comprises a main body, wherein the receptacle may be detachable from the main body to enable an exchange of the cartridge. In particular, a used cartridge may be removed and a new one may be inserted. Preferably, when the receptacle is detached, a movement of the guide member, in particular a rotation of a nut member may be enabled. Thereby, a reset of the piston rod to the start position may be enabled. Accordingly, the drive assembly may be switched from its operational state to its reset state by the detachment of the receptacle. The piston rod may have to be in the start position when a medication receptacle holding a new cartridge is attached to the main body. The piston rod may be in the end position when the medication from the cartridge has been fully or partially dispensed.

Preferably, the impeding element is configured to inhibit an unhindered rotation of the guide member, when the receptacle is detached from the main body. Thereby, the impeding element may inhibit an unhindered movement of the piston rod from the end position to the start position when the receptacle is detached from the main body. In particular, an accidental movement of the piston rod may be prevented. As an example, an unintended movement of the piston rod during an accidental detachment of the receptacle may be prevented.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ωcarboxyheptadecanoyl)-des(B30) human insulin and B29-N-(ω-carboxyheptadecanoyl) human insulin.

Exendin-4 for example means Exendin-4(1-39), a peptide of the sequence H-His -Gly-Glu-Gly-Thr-Phe-Thr-Ser-Asp-Leu-Ser-Lys-Gln-Met-Glu-Glu-Glu-Ala-Val-Arg-Leu-Phe -Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4 (1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02) 25, Asp28] Exendin-4(1-39)-NH2,
des Pro36, Pro37, Pro38 [Met(O)14, Trp(02)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

DETAILED DESCRIPTION

Figure 1:
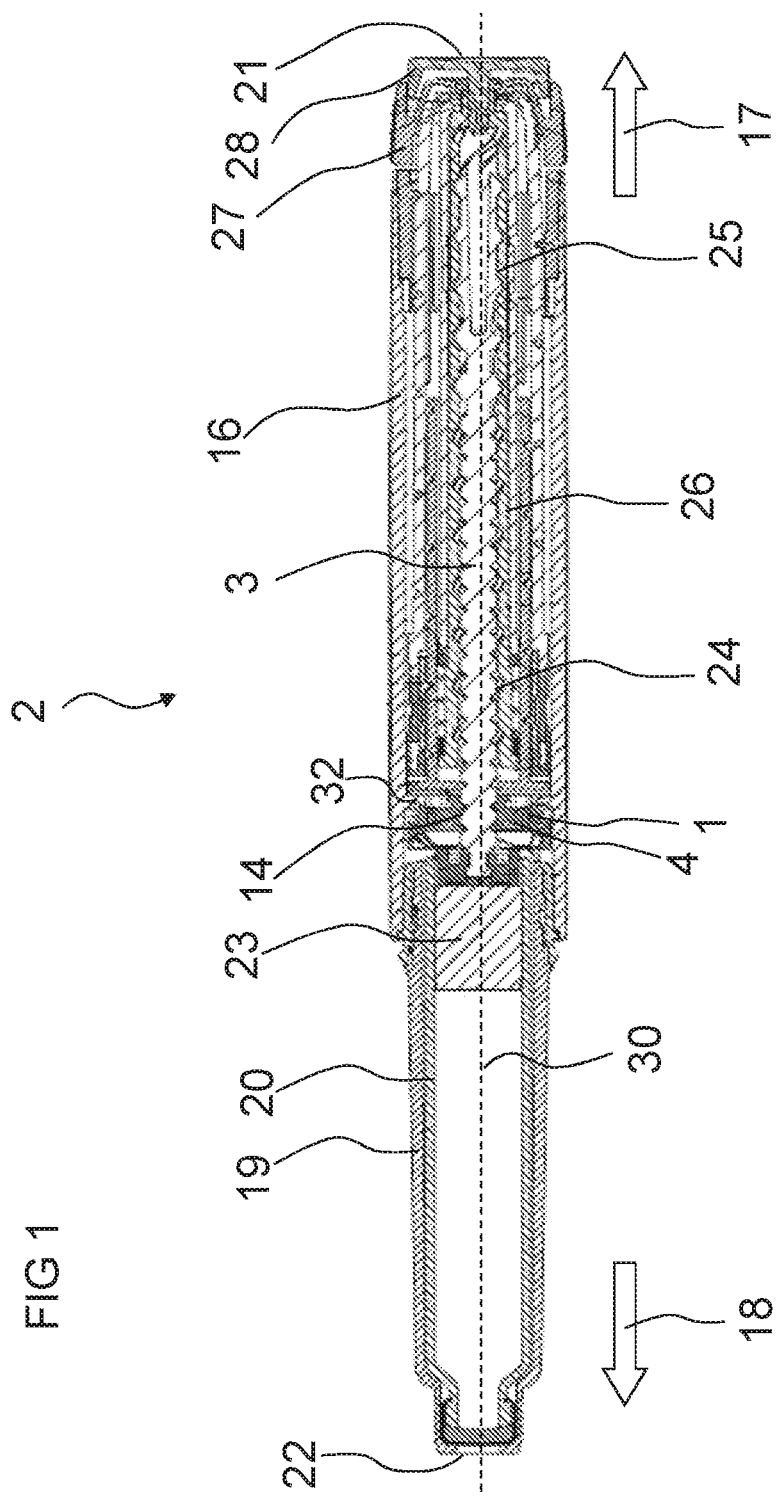
FIG. 1 shows a cross-sectional view of a medication delivery device comprising a drive assembly.

FIG. 1 shows a medication delivery device 2, in particular an injection device. For the detailed description of the medication delivery device 2 it is referred to WO 2009/132778 A1. The medication delivery device 2 comprises a drive assembly 1 comprising a piston rod 3 and a guide member 4.

The piston rod 3 acts on a piston 23 in a cartridge 20 containing a medication. The cartridge 20 is located in a receptacle 19. The receptacle 19 is attached to a main body 16 of the medication delivery device 2.

The piston rod 3 is configured as a lead screw. The lead screw comprises two threaded sections 24, 25. The threaded sections 24, 25 have opposite senses of rotation. A first threaded section 24 is located at a distal part of the piston rod 3 and a second threaded section 25 is located at a proximal part of the piston rod 3. The piston rod 3 is in threaded engagement with the guide member 4 with the first threaded section 24. Furthermore, with the second threaded section 25, the piston rod 3 is in threaded engagement with a drive member 26. In a dose delivery operation, the drive member 26 exerts a force on the piston rod 3, thereby causing a movement of the piston rod 3.

The medication delivery device 2 comprises a dose setting member 27 and a dispense button 28. For setting a dose, the dose setting member 27 is rotated until the desired dose has been reached. For dispensing the set dose, the dispense button 28 is depressed.

During a dispense operation, the piston rod 3 is moved in a distal direction 18, towards a distal end 22 of the medication delivery device 2. The distal end 22 is the dispensing end of the medication delivery device 2. In particular, during dose delivery, the piston rod 3 is rotated through the guide member 4 towards the distal end 22.

In the depicted embodiment, the piston rod 3 is shown in a start position and the drive assembly 1 is in an operational state. During the delivery of a dose of a medication, the piston rod 3 is moved towards an end position. The start position may be the most proximal position of the piston rod 3. The end position may be the most distal position of the piston rod 3. In particular, the piston rod 3 may have reached the end position when the medication in the cartridge 20 has been fully or partially delivered.

After one or several dispense operations, the piston rod 3 may be reset to the start position for enabling a reuse of the device. In particular, the piston rod 3 may be moved in a proximal direction 17, towards a proximal end 21 of the medication delivery device 2.

The medication delivery device 2 comprises a locking mechanism for preventing a rotation of the guide member 4 with respect to the main body 16 when the receptacle 19 is attached to the main body 16. Thereby, a movement of the piston rod 3 in a proximal direction may be inhibited due to a blocking by the two threaded sections 24, 25 being in engagement with the guide member 4 and the drive member 26, respectively.

When the receptacle 19 is detached from the main body 16, the guide member 4 is disengaged from the main body 16, such that a rotation of the guide member 4 is enabled. In particular, the guide member 4 is enabled to rotate with respect to a longitudinal axis 30 of the medication delivery device 2. Thereby, the drive assembly 1 switches from its operational state as shown in FIG. 1 into its reset state, wherein a reset of the piston rod 3 back to the start position is enabled. During a reset, the piston rod 3 is rotated towards the proximal end 21. A movement of the guide member 4 in proximal direction 17 is blocked by a body part 32 such that the guide member 4 rotates with respect to the body part 32 and with respect to the piston rod 3 during a reset of the piston rod 3.

The drive assembly 1 comprises an impeding element, which is not shown in FIG. 1 for clarity reasons. The impeding element is configured to impede a rotation of the guide member 4 after a detachment of the receptacle 19, i.e. in the reset state of the drive assembly 1. Thereby, an increased force is required for rotating the guide member 4 and thereby, for resetting the piston rod 3. Thereby, an unintended movement of the piston rod 3, for example by the gravitational force of the piston rod 3, may be prevented, for example during an accidental detachment of the receptacle 19.

Figure 2:
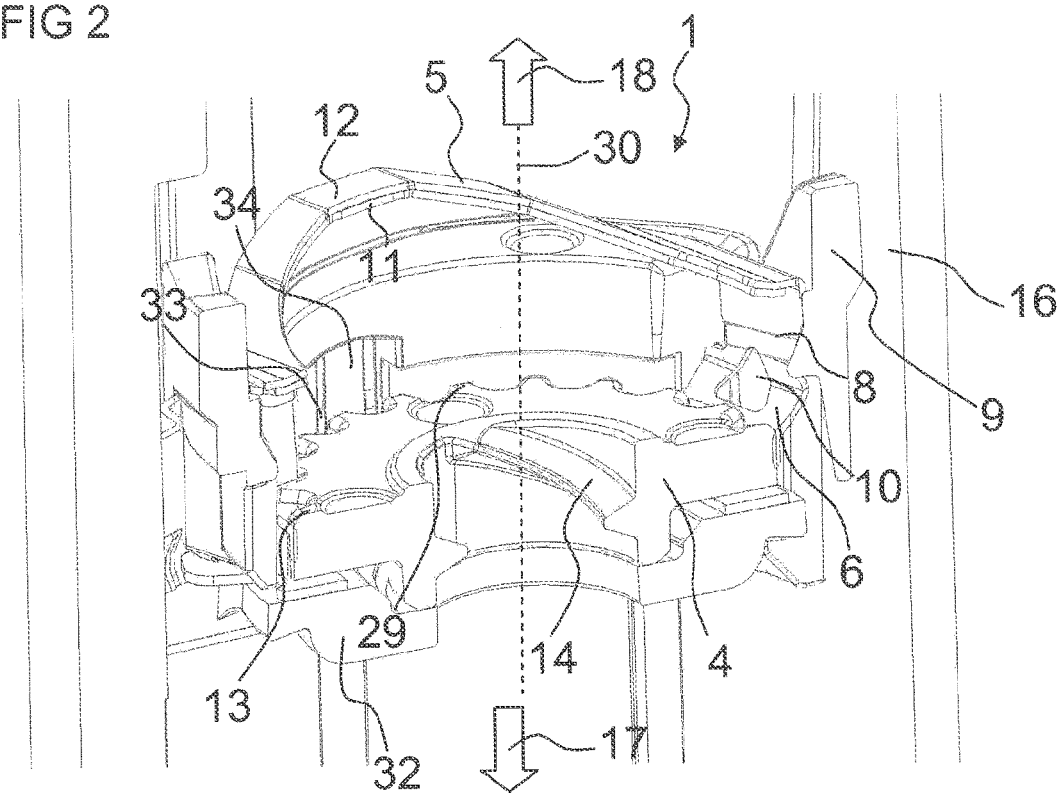
FIG. 2 shows a perspective sectional view of a part of a drive assembly comprising an impeding element and a guide member.
Figure 3:
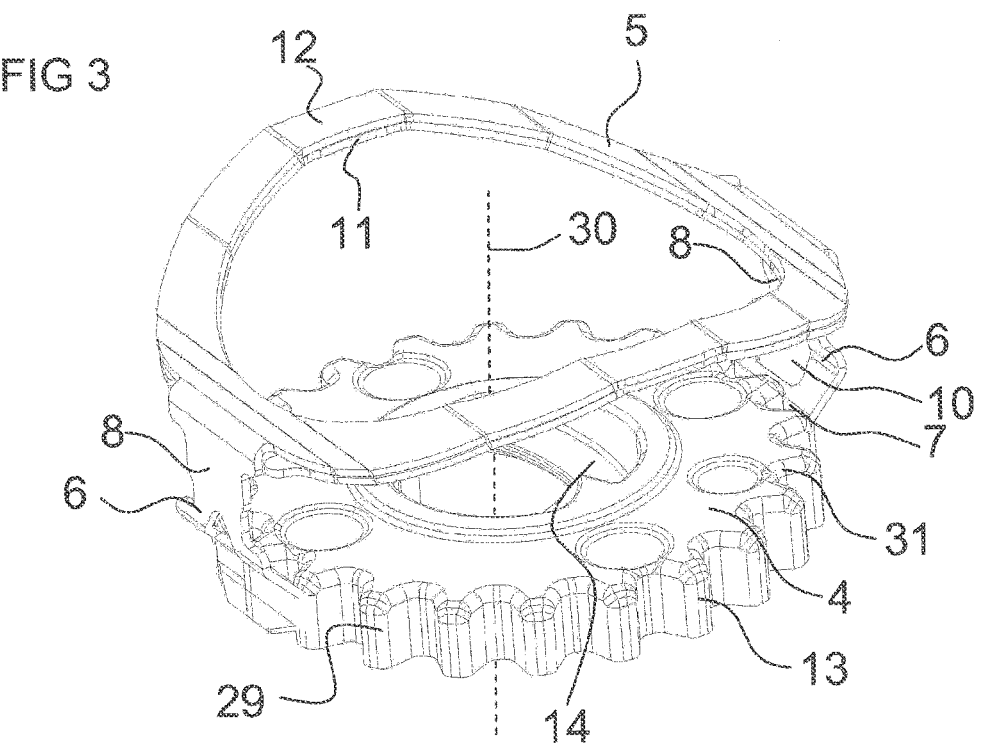
FIG. 3 shows a perspective view of the impeding element assembled with the guide member of FIG. 2.

FIG. 2 shows an impeding element 5 and the guide member 4 assembled in a drive assembly 1 of a medication delivery device, for example the device 2 shown in FIG. 1. FIG. 3 shows a detailed view of the impeding element 5 and the guide member 4 assembled in a drive assembly 1.

As can be seen in FIGS. 2 and 3, the guide member 4 comprises an internal thread 14. The thread 14 of the guide member 4 is configured to be in engagement with a piston rod. The piston rod is not shown for clarity reasons.

The body part 32 of the drive assembly 1 is permanently fixed to the main body 16 of the device 2. The drive assembly 1 comprises a locking member 33 for rotationally locking and unlocking the guide member 4 with respect to the body part 32 of the drive assembly 1 and, thereby, with respect to the main body 16 of the device 2. The locking member 33 may be a spring member. The spring member may comprise a hooked end and may be biased towards the guide member 4.

In particular, the locking member 33 engages with an engagement member 13 of the guide member 4 for preventing a rotational movement of the guide member 4 during a dispense operation. The engagement member 13 comprises a plurality of teeth 29 located at the circumference 31 of the guide member 4. The teeth 29 are configured to inhibit a rotation of the guide member 4 when being in engagement with the locking member 33 of the drive assembly 1.

Furthermore, the locking mechanism comprises a turning ring 9. The turning ring 9 is configured to cause an engagement and a disengagement of the locking member 33 with the engagement member 13. Accordingly, the turning ring 9 is configured to switch the drive assembly 1 from the operational state to the reset state and vice versa. The turning ring 9 is engaged with the main body 16, such that it is rotatable about a predefined angle with respect to the main body 16.

The turning ring 9 comprises at least one opening 34. When the opening 34 is aligned with the locking member 33, the locking member 33 extends through the opening and engages with the teeth 29. The locking member 33 of the drive assembly 1 may be configured to extend through the opening 34 in an operational state of the drive assembly. In particular, when the receptacle is attached to the main body 16, the locking member 33 engages with the engagement member 13 of the guide member 4, and thereby prevents a rotation of the guide member 4.

When the medication receptacle is detached from the main body 16, the turning ring 9 is rotated about a predefined angle with respect to the main body 16. Thereby, also the opening 34 of the turning ring 9 is rotated. In particular, the opening 34 is rotated such that the locking member 33 is disengaged from the guide member 4. Thereby, a rotation of the guide member 4 and, thus, a reset of the piston rod is enabled.

During an attachment of the receptacle to the main body 16, the turning ring 9 and, thereby, the opening 34, is rotated such that the opening 34 is aligned with the locking member 33. Thus, the locking member 33 extends through the opening 34 and engages with the teeth 29 of the engagement member 13. Thereby, the guide member 4 is rotationally fixed with respect to the main body 16 during an operational state.

A movement of the guide member 4 in a proximal direction 17 is prevented by the body part 32 extending radially from the main body 16. A movement of the guide member 4 in a distal direction 18 is prevented by the turning ring 9.

For increasing a force required for resetting the piston rod, the drive assembly 1 comprises an impeding element 5 being in contact with the guide member 4. The impeding element 5 comprises the shape of a bended ring with two lateral arms 8.

The bended ring is configured to bias the cartridge towards the distal end of the receptacle, when the receptacle is attached to the medication delivery device. In particular, the bended ring is configured to fix the cartridge in the receptacle during dose delivery.

The impeding element 5 is fixed with respect to the turning ring 9 by the two lateral arms 8. In particular, the lateral arms 8 are snap-fitted to the turning ring 9. In particular, the impeding element 5 is rotationally fixed with respect to the turning ring 9, and, thereby rotationally fixed with respect to the main body 16 of the device 2 at least during a reset of the piston rod 3.

The impeding element 5 comprises two resilient elements 6 being provided by the lateral arms 8. The resilient elements 6 comprise contact surfaces 7 being in contact with the guide member 4.

In particular, the resilient elements 6 are pretensioned towards the guide member 4. Thereby, the resilient elements 6 of the impeding element 5 exert a force on the guide member 4. In particular, the resilient elements 6 exert a radial force on the guide member 4, with respect to the longitudinal axis 30. The force exerted on the guide member 4 by the resilient elements 6 may be an elastic force. During a movement of the guide member 4, the elastic force may cause a friction force being exerted on the guide member 4. Furthermore, during a movement of the guide member 4, the resilient elements 6 slide over the teeth 29. Thereby, also an elastic force has to be overcome. Thereby, a rotation of the guide member 4 is impeded. In particular, a force required for rotating the guide member 4 is increased.

Figure 4:
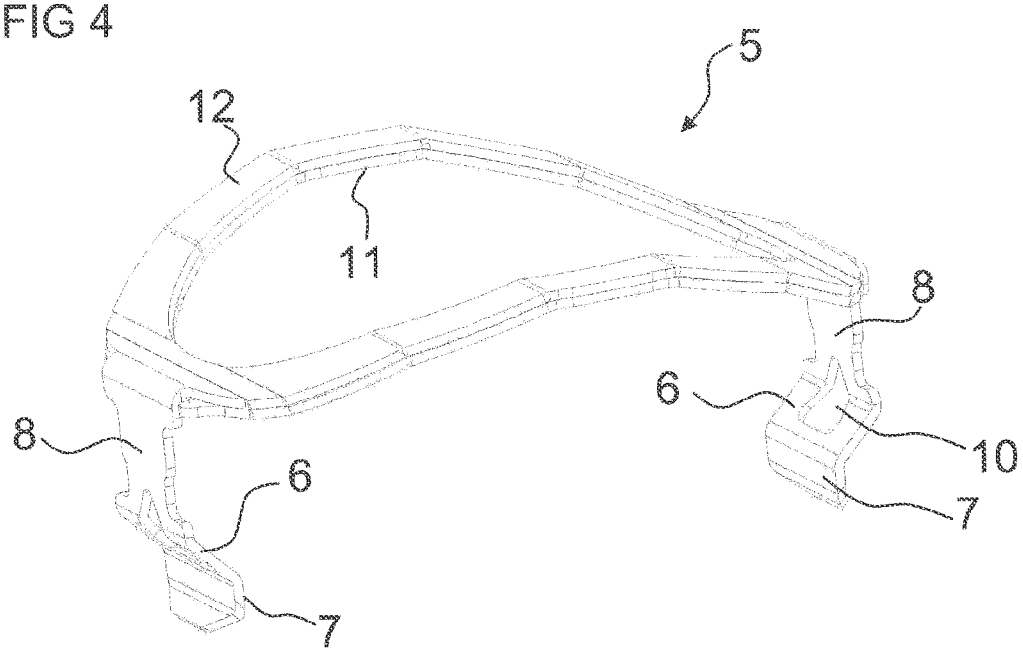
FIG. 4 shows a perspective view of the impeding element of FIG. 2.
Figure 5:
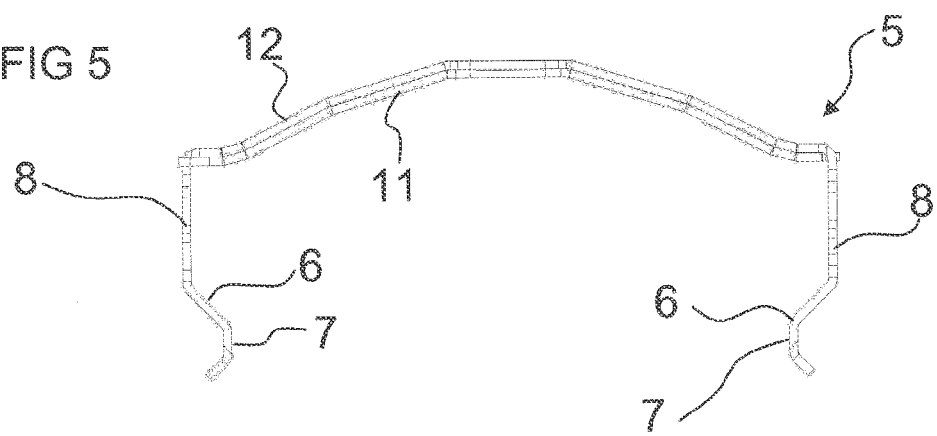
FIG. 5 shows a side view of the impeding element of FIG. 2.
Figure 6:
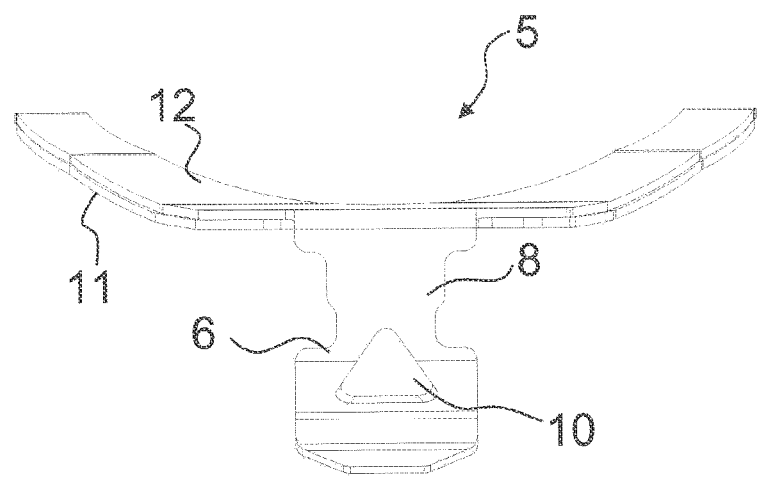
FIG. 6 shows a side view of the impeding element of FIG. 2 from a different direction than shown in FIG. 5.

FIG. 4 shows a perspective view of the impeding element 5 of FIG. 2. FIG. 5 shows a side view of the impeding element 5 of FIG. 2. FIG. 6 shows a side view of the impeding element 5 which is rotated by 90° compared to the side view of FIG. 5.

The impeding element 5 comprises a lower part 11 and an upper part 12. The lower part 11 is configured to reinforce the impeding element 5 and, thereby, increase the stability of the impeding element 5.

The lower part 11 of the impeding element 5 comprises the shape of a bended ring. The upper part 12 of the impeding element 5 comprises the shape of a bended ring with two lateral arms 8. The lateral arms 8 are configured to rotationally fix the impeding element with respect to the turning ring 9 shown in FIG. 2.

The resilient elements 6 of the impeding element 5 are located opposite to each other. Each resilient element 6 comprises a cut-out 10. The elasticity of the resilient element 6 may be determined by the shape of the cut-out 10. Particularly, the amount of the force exerted on the guide member 4 by the resilient elements 6 may be affected by the shape of the cut-out 10. In the depicted embodiment, the cut-out 10 comprises the shape of a triangle.

The resilient element 6 of the impeding element 5 comprises a contact surface 7. The contact surface 7 is configured to be in contact with the guide member 4 of the drive assembly 1 as shown in FIG. 2.

The contact surface 7 of each resilient element 6 is at least as wide as a gap between two engagement members 13 of the guide member 4. Thereby, a jamming of the resilient elements 6 in the gap between two engagement members 13 of the guide member 4 is inhibited. For example, a jamming between two teeth of the guide member 4 is inhibited.

The invention claimed is:

1. A drive assembly for a medication delivery device, comprising
    a piston rod movable from a start position to an end position for medication delivery and resettable from the end position to the start position,
    a guide member being in engagement with the piston rod;
    a body part; and
    an impeding element for impeding a movement of the guide member during a reset of the piston rod, thereby impeding the reset of the piston rod,
    wherein during a movement of the piston rod towards the end position the guide member is rotationally fixed with respect to the body part,
    wherein during the reset of the piston rod towards the start position the guide member is rotationally movable with respect to the body part.

2. The drive assembly of claim 1, wherein the guide member and the piston rod are threadedly engaged.

3. The drive assembly of claim 1, wherein the impeding element comprises at least one resilient element.

4. The drive assembly of claim 1, wherein the impeding element comprises a contact surface being in contact with the guide member.

5. The drive assembly of claim 1, wherein the impeding element is biased towards the guide member.

6. The drive assembly of claim 1, wherein the impeding element comprises a cut-out affecting an elasticity of the impeding element.

7. The drive assembly of claim 1, wherein the guide member comprises at least one engagement member being configured to rotationally fix the guide member to the body part during medication delivery.

8. The drive assembly of claim 7, wherein the impeding element is configured to not engage with the engagement member.

9. The drive assembly of claim 1 further characterized in that the impeding element is formed as a bended ring with two lateral arms extending therefrom.

10. A drive assembly for a medical delivery device comprising:
    a piston rod movable from a start position to an end position for medication delivery and resettable from the end position to the start position,
    a guide member being in engagement with the piston rod;
    a body part; and
    an impeding element for impeding a movement of the guide member during a reset of the piston rod, thereby impeding the reset of the piston rod,
    wherein during a movement of the piston rod towards the end position the guide member is rotationally fixed with respect to the body part,
    wherein the guide member comprises at least one engagement member being configured to rotationally fix the guide member to the body part during medication delivery, and
    wherein the impeding element is configured to not engage with the engagement member.

11. A medication delivery device comprising:
    a main body, wherein a receptacle is detachable from the main body to enable an exchange of a cartridge containing a medicament;
    a piston rod movable from a start position to an end position for medication delivery and resettable from the end position to the start position,
    a guide member being in engagement with the piston rod;
    a body part; and
    an impeding element for impeding a movement of the guide member during a reset of the piston rod, thereby impeding the reset of the piston rod,
    wherein the impeding element is configured to inhibit an unhindered resetting of the piston rod when the receptacle is detached from the main body.

* * * * *